United States Patent
Maitra et al.

(10) Patent No.: US 10,106,830 B2
(45) Date of Patent: Oct. 23, 2018

(54) METHODS OF DETECTING AND QUANTIFYING BACTERIA CONTAINED ON OR WITHIN CHEWING GUM

(71) Applicant: WM. WRIGLEY JR. COMPANY, Chicago, IL (US)

(72) Inventors: Amarnath Maitra, Chicago, IL (US); Stefan Wessel, Thesinge (NL); Henny C. Van Der Mei, Groningen (NL); Henk J. Busscher, Thesinge (NL)

(73) Assignee: WM. WRIGLEY JR. COMPANY, Chicago, IL (US)

( * ) Notice: Subject to any disclaimer, the term of this patent is extended or adjusted under 35 U.S.C. 154(b) by 0 days.

(21) Appl. No.: 15/110,903

(22) PCT Filed: Jan. 9, 2015

(86) PCT No.: PCT/US2015/010725
§ 371 (c)(1),
(2) Date: Jul. 11, 2016

(87) PCT Pub. No.: WO2015/106049
PCT Pub. Date: Jul. 16, 2015

(65) Prior Publication Data
US 2016/0326565 A1    Nov. 10, 2016

Related U.S. Application Data

(60) Provisional application No. 61/925,941, filed on Jan. 10, 2014.

(51) Int. Cl.
  *C12Q 1/00*    (2006.01)
  *C12Q 1/04*    (2006.01)
  *C12Q 1/70*    (2006.01)

(52) U.S. Cl.
  CPC ............. *C12Q 1/04* (2013.01); *C12Q 1/70* (2013.01)

(58) Field of Classification Search
  CPC ........................................................ C12Q 1/04
  See application file for complete search history.

(56) References Cited

U.S. PATENT DOCUMENTS 3,691,151 A * 9/1972 Guadagnini ......... C07H 15/234
                                                      536/13.7
2009/0074910 A1* 3/2009 Steinberg ............... A23G 4/06
                                                           426/3

FOREIGN PATENT DOCUMENTS

EP    0213059 A2    3/1987
WO    2014159901 A2   10/2014

OTHER PUBLICATIONS

Almaguer-Flores et al., "Oral Bacterial Adhesion on Amorphous Carbon and Titanium Films: Effect of Surface Roughness and Culture Media", Journal of Biomedical Materials Research, Jan. 1, 2010, vol. 92B, No. 1, pp. 196-204.
Wessel et al., "Quanitification and Qualification of Bacteria Trapped in Chewed Gum", PLOS ONE, Jan. 20, 2015, vol. 10, No. 1, 9 pages.

* cited by examiner

*Primary Examiner* — Albert M Navarro (57) ABSTRACT

The invention provides for methods of extracting and quantitating the number of microorganisms contained on or within in chewing gum.

11 Claims, 2 Drawing Sheets

METHODS OF DETECTING AND QUANTIFYING BACTERIA CONTAINED ON OR WITHIN CHEWING GUM

CROSS-REFERENCE TO RELATED APPLICATIONS

This application is a U.S. National Phase Patent Application of International Application Serial Number PCT/US2015/010725, filed Jan. 9, 2015, which is incorporated herein in its entirety, and which claims priority benefit of U.S. Provisional Patent Application Ser. No. 61/925,941, filed on Jan. 10, 2014, the entire contents of which is also incorporated herein by reference.

FIELD OF INVENTION

The invention provides for methods of extracting and quantitating the number of microorganism contained on or within chewing gum.

BACKGROUND

Descriptions of the first use of chewing gum date back to the ancient Greek, where people used tree resins from the mastic tree to quench thirst or freshen ones breath. The first chewing gum was not successfully marketed until the late 19th century, when the rubbery tree sap of the Sapodilla tree formed the basis of the gum. In the late 20th century, chewing gum is not only regarded as a symbol of life style, but also effects on cognitive performance, mood, alertness and appetite control have been reported. Moreover, chewing gum has developed more towards an oral care and functional food product ("nutriceutical") as it provides an easily applicable drug delivery vehicle with potential benefits for oral health. High consumption rates, up to 2.5 kg per person per year, have made it into a billion dollar industry.

Generally, chewing gums consist of a water insoluble mixture of synthetic elastomers, like polyvinyl acetate or polyisobutylene, generally referred to as the gum-base. Important requirements to gum-base materials are that they do not dissolve in the mouth and can be chewed for long periods of time without undergoing compositional changes. In all commercially available chewing gums, the gum-base is supplemented with structuring, softening and flavoring agents, while nowadays sugar is frequently replaced by artificial sweeteners such as sorbitol, xylitol or mannitol.

The inclusion of xylitol and other artificial sweeteners has been described to reduce the formation of oral biofilms on teeth. Oral biofilms are causative to the world's most widespread infectious diseases, namely caries and periodontal disease. Caries arise from an imbalance between naturally occurring de- and remineralization of dental enamel. Demineralization occurs when the pH of oral biofilm drops below 5.5 due to the fermentation of sugars by selected members of oral biofilms on teeth. Most artificial sugars are not or barely fermented by oral bacteria and therewith do not lower the pH. Moreover, chewing gum yields enhanced mastication that stimulates saliva production, therewith increasing the concentrations of calcium and phosphates in the oral cavity required for remineralization. Fluorides have been added to commercial gums to prevent enamel demineralization and stimulate remineralization. It is tempting to regard the chewing of gum as an addendum to daily oral hygiene procedures, especially since most people have through the ages been unable to maintain a level of oral biofilm control required to prevent disease. This has led to the incorporation of antimicrobials like chlorhexidine and herbal extracts to chewing gums and gums have indeed been demonstrated successful in preventing re-growth of oral biofilm. Although it is known that chewing of gum aids removal of interdental debris (Kakodkar et al. Dental Research Journal 7: 64-69, 2011) and detergents like polyphosphates have been added to gums to increase their cleaning power, it is unclear whether chewing of gum will actually remove bacteria from the oral cavity. Especially the preferential removal of disease-causing organisms like acid-producing *Streptococcus mutans* or species that are regarded as initial colonizers to the dental enamel by chewing gum would turn chewing gum into a valuable addendum to daily oral hygiene procedures.

The human oral cavity contains a varied and vast amount of flora, and many diseases of the gastrointestinal system and respiratory system can manifest in the oral cavity. There are also many diseases that are specific to the oral cavity. In addition to bacterial organisms, oral microorganisms can include fungal, protozoan, and viral species and many of these microorganisms adhere to the teeth, the gingival sulcus, the tongue, and the buccal mucosa. Each site has a unique way of allowing bacteria to establish their residency. Each site has a unique way of allowing the organisms to establish their residency. Many of these microorganisms may adhere to and become entrapped in polymers that they contact while in the oral cavity, and these polymers include dental and periodontal apparatus and compositions in addition to chewing gum as described above.

Therefore, there is a need for the development of new methods to detect, identify and quantify the numbers of microorganisms that adhere to polymers in the oral cavity, such as bacteria that are contained on or within chewing gum after use.

SUMMARY OF INVENTION

Chewing gum is known to contribute towards maintenance of oral health; however it is unclear whether gum can actually remove bacteria and other microorganisms from the oral cavity. The present invention provides a method for detecting and quantitating microorganisms that are contained on and within the chewing gum after use (e.g. in vivo chewing, finger chewing, or robotic or artificial stimulated chewing). The studies provided herein describe a method by which the number of microorganisms contained on and within the gum after chewing were quantified and qualified.

The invention provides for methods of detecting and quantitating the number of microorganism contained on or within chewing gum. The term "contained" refers to microorganisms that are attached or adhered to the chewing gum including microorganisms that are within or entrapped in the folds of masticated or finger-chewed chewing gum.

In one aspect of the invention, the invention provides for methods of detecting a microorganism contained on or within chewing gum comprising a) sonicating the chewing gum under conditions which remove the microorganism from the chewing gum and deposit the microorganism in a suspension, b) contacting at least a portion of the suspension with a solid-support under conditions that promote colony formation, wherein the formation of a colony on the solid-support indicates the presence of a microorganism contained on or within the chewing gum. In this method, the chewing gum can be contacted to an oral cavity of a mammal prior to sonication such as the mammal chewed the gum, or the microorganism attached to the chewing gum outside of the oral cavity of mammal, such as by finger chewing as described in Example 1 or by mechanical or robotic chewing stimulators A "solid-support" is a matrix in which a microorganism, such as a bacteria, fungus, protozoa or virus can grow on such as media comprising agar or another inert solidifying agent such as gelatin.

Sonication refers to the act of applying sound energy, such as ultrasound, to agitate particles in a samples, e.g. sonicate chewing gum to remove a microorganism, such as a bacteria attached thereto. Some sonicators utilize a probe that directly contacts the sample. Water bath based sonicators have ultrasound generating elements located below the tank which indirectly agitate the sample. The sonication must be carried out in standardized dimensions, such as sonicating chewing gum that was formed to a particular shape using a mold. The mold may be any shape with standardized dimensions and may be of any material which only slightly or does not adhere chewing gum such as polytetrafluoroethylene (TEFLON).

The methods of detecting a microorganism contained on or within chewing gum may further comprise a step of quantifying the microorganisms contained on or within masticated chewing gum, wherein the number of colonies is indicative of the quantity of microorganisms contained on and within the chewing gum. The quantification may comprise generating a standard curve to determine the quantity of microorganisms contained on or within the chewing gum. The combination of sonicating the chewing gum and the generation of the standard curve allows for using the number of microorganisms on the surface of the chewing gum to extrapolate the total number of microorganism contained on or within the chewing gum.

In another aspect of the invention, the invention provides for methods of detecting the presence of a microorganism in the oral cavity of a mammal comprising a) sonicating chewing gum that was in contact with the oral cavity of a mammal under conditions which remove the microorganism from the chewing gum and deposit microorganism in a suspension, b) contacting at least a portion of the suspension with a solid-support under conditions that promote colony formation, wherein the formation of a colony on the solid-support indicates the presence of a microorganism in the oral cavity of the mammal. The sonication may be carried out in standardized dimensions, such as sonicating chewing gum that was formed to a particular shape using a mold.

The methods of detecting the presence of a microorganism in the oral cavity of a mammal may further comprise the step of quantifying the microorganism contained within the oral cavity of the mammal, wherein the number of colonies is indicative of the quantity of microorganisms within the oral cavity of the mammal. The quantification may comprise generating a standard curve to determine the quantity of microorganisms within the oral cavity of the mammal.

In another aspect of the invention, the invention provides for methods of quantitating microorganisms contained on or within chewing gum comprising a) sonicating the chewing gum under conditions which remove the microorganisms from the chewing gum and deposit the microorganisms in a suspension, b) contacting at least a portion of the suspension with a solid-support under conditions that the promote colony formation, and c) quantitating the colonies formed on the solid-support, wherein the number of colonies indicates the quantity of microorganisms contained on and within the chewing gum. The methods of quantitating microorganisms attached to chewing gum may further comprise the step of generating a standard curve to determine the quantity of microorganisms attached to the chewing gum. The sonication may be carried out in standardized dimensions, such as sonicating chewing gum that was formed to a particular shape using a mold.

Any of the above-described methods may further comprise the step of identifying the microorganism. These microorganisms include bacteria, virus, fungus and protozoa. For example, bacteria that are detected and quantified by the methods of the invention include pathogenic or commensal bacteria of the oral cavity such as *Streptococcus mutans, Streptococcus oralis, Actinomyces naeslundii, Streptococcus sanguinis, Porphyromomas gingivalis, Porphymomas intermedia, Bacteroides forsythus, Tanneraella forsythia, Campylobacter rectus, Eubacerium nodatum, Peptostreptococcus micros, Streptococcus intermedius, Aggregetibacter actinomycetemcomitans, Treponema denticola, Eikenella corrodens, Capnocytophaga gingivalis, Streptococcus gordonii, Veillonella parvula, Fusobacterium nucleatum, Prevotella intermedia, Lactobacillus salivarius, Streptococcus salivarius* and *Streptoococus sobrinus*.

In addition, any of the above-described methods of the invention may further comprise the step of diagnosing a microorganism infection in a mammalian subject wherein the chewing gum was in contact with the oral cavity of the subject and wherein the presence of a microorganism contained on or within chewing gum is indicative of a microorganism infection in the subject.

Another aspect of the invention provides for methods of generating a microorganism profile of the oral cavity of a mammalian subject comprising a) contacting chewing gum with the oral cavity of the subject, b) detecting the presence and absence of at least one microorganism contained or within the malleable polymer after contact with the oral cavity of the subject, wherein the presence or absence of at least one type of microorganism determines the microorganism profile of the oral cavity of the subject. When the malleable polymer is chewing gum, the microorganism may be contained on the chewing gum or contained within the folds of masticated or finger-chewed chewing gum. The term "type of microorganism" refers to a single family, genus, species, strain, serotype or serogroup of microorganism depending on identification method. This microorganism may be a bacteria, virus, fungus or protozoa. The microorganism profile may comprise information on at least one type of microorganism, at least two types of microorganisms, at least five types of microorganisms, at least 10 types of microorganism, at least 20 types of microorganisms, at least 50 types of microorganisms, at least 100 types of microorganisms or at least 500 types of microorganisms. The profile may comprise only type of microorganisms or multiple different types of microorganisms In particular, the invention provides for "bacterial profiles" that comprise information on at least one type of bacteria, at least two types of bacteria, at least five types of bacteria, at least 10 types of bacteria, at least 20 types of bacteria, at least 50 types of bacteria, at least 100 types of bacteria or at least 500 types of bacteria.

The invention also provides for viral profile that comprises information on at least one type of virus, at least two types of virus, at least five types of virus, at least 10 types of virus, at least 20 types of virus, at least 50 types of virus, at least 100 types of virus and at least 500 types of virus.

In addition, the invention provides for microorganism profiles that comprise information on at least one type of fungus (fungal profile), at least two types of fungi, at least five types of fungi, at least 10 types of fungi, at least 20 types of fungi, at least 50 types of fungi, at least 100 types of fungi or at least 500 types of fungi.

In addition, the invention provides for microorganism profiles that comprise information on at least one type of protozoa (protozoan profile), at least two types of protozoa, at least five types of protozoa, at least 10 types of protozoa, at least 20 types of protozoa, at least 50 types of protozoa, at least 100 types of protozoa or at least 500 types of protozoa.

These methods may optionally further comprise the steps of comparing the microorganism profile of the mammalian subject with a reference microorganism profile, wherein the reference profile is indicative of increased susceptibility for a disease, disorder or condition of the oral cavity and scoring the microorganism profile to determine whether the subject has increased susceptibility for a disease or disorder of the oral cavity. Further, these methods may optionally comprise a step of quantitating the microorganisms contained on and within the chewing gum.

The term "microorganism profile" refers to the presence or absence of at least one type of microorganism that is at least partially identified or characterized so that the presence or absence of the microorganism in any particular sample may be monitored. The term "microorganism profile" includes bacterial profiles, viral profiles, protozoan profiles and fungal profiles and combinations thereof. The term "reference microorganism profile" refers to a microorganism profile generated for a known control or standard sample, such as a reference profile for a subject known to have increased susceptibility for a disease, disorder or condition of the oral cavity. For example, the microorganism profile may comprise one or more types of bacteria, one or more types of fungi, one or more types of protozoa or one or more types of virus. Furthermore, the microorganism profile may comprise a combination of the microorganisms such as one or more types of bacteria, virus, fungi and/or protozoa.

A microorganism profile of a subject associates with a reference bacterial profile when one or more the microorganisms in the reference profile are present in the microorganism profile of the subject. To determine if a subject microorganism profile associates with a reference microorganism profile, the profiles are scored to compare the subject microorganism profile with the reference profile.

The term "bacterial profile" refers to the presence or absence of at least one type of bacteria that is at least partially identified or characterized so that the presence or absence of the bacteria in any particular sample may be monitored. The term "reference bacterial profile" refers to a bacterial profile generated for a known control or standard sample, such as a reference profile for a subject known to have increased susceptibility for a disease, disorder or condition of the oral cavity.

A bacterial profile of a subject associates with a reference bacterial profile when one or more the bacteria in the reference profile are present in the bacterial profile of the subject. To determine if a subject bacterial profile associates with a reference bacterial profile, the profiles are scored to compare the subject microbe profile with the reference profile.

The methods of generating a bacterial profile may detect one or more of type of bacteria. For example, the bacteria detected to generate a bacterial profile include *Streptococcus mutans*, *Streptococcus oralis*, *Actinomyces naeslundii*, *Streptococcus sanguinis*, *Porphyromomas gingivalis*, *Porphymomas intermedia*, *Bacteroides forsythus*, *Tanneraella forsythia*, *Campylobacter rectus*, *Eubacerium nodatum*, *Peptostreptococcus micros*, *Streptococcus intermedius*, *Aggregetibacter actinomycetemcomitans*, *Treponema denticola*, *Lactobacillus*, *Eikenella corrodens*, *Capnocytophaga gingivalis*, *Streptococcus gordonii*, *Veillonella parvula*, *Fusobacterium nucleatum*, and *Streptoococus sobrinus*, to name a few.

Furthermore, any of the microorganism profiles of the present invention may be used to determine susceptibility of the subject for developing a disease, condition or disorder such as chronic periodontitis, acute adult periodontitis, gingivitis such as acute necrotizing ulcerative gingivitis, Vincent angina (trench mouth), dental caries, herpesvirus infection, primary herpetic gingivostomatitis or oral herpes (cold sores and canker sores), genital herpes, varicella-zoster virus infection e.g. chicken pox or shingles, influenza, common cold, venereal disease, mononucleosis, coxsackievirus infection such as hand-foot-mouth disease, herpangina, acute lymphonodular pharyngitis, mumps, measles (reubeola), rubella (German measles), African Burkitt lymphoma, nasopharyngeal carcinoma, oral hairy leukoplakia, roseola infantum, Karposi sarcoma, Candidiasis, acute pseudomemranous candidosis (thrush), acute atrophic (erythematous) candidosis, chronic hyperplastic candidosis, chronic atrophic (erythematous) candidosis, aspergillosis, cryptococcosis, histoplasmosis, blastomycosis, paracoccidioidomycosis, and zygomycosis (mucormycosis).

In another aspect, the invention provides for kits for carrying out any of the preceding methods described herein. In particular, the invention provides kits for detecting or quantitating microorganisms contained on or within masticated chewing gum or for generating a bacterial profile in a mammalian subject.

DESCRIPTION OF DRAWING

FIG. 1 provides a calibration curve for the finger chewed gum, described in Example 1. The curve depicts the amount of bacteria retrieved after finger-chewing expressed over the starting amount of bacteria finger chewed-in.

DETAILED DESCRIPTION

The invention provides for method of detecting and quantifying microorganism, such as bacteria, contained on or entrapped within masticated chewing gum using sonication to remove the microorganism from the chewing gum. The term "contained" refers to microorganisms that are attached or adhered to the chewing gum including microorganisms that are within or entrapped in the folds of masticated or finger-chewed chewing gum. In particular, the invention provides for methods of detecting and quantitating bacteria contained on and within masticated chewing gum using sonication to remove the bacteria from the chewing gum and depositing the bacteria on a solid-support under conditions that promote colony growth, wherein the formation of a bacterial colony on the solid-support indicates the presence of bacteria contained on or within the chewing gum. The number of colonies formed allows for the generation of a standard calibration curve as described in Example 1. This method consistently determines the number of bacteria contained on and within chewing gum independent of type of bacteria or type of gum tested. As sonication can only release bacteria attached to the surface of the chewing gum, the number of bacteria retrieved is roughly 1 log-unit less than chewed in.

The use of the calibration curve allows for the calculation of the number of bacteria contained on or contained within the gum. Specifically, the combination of sonicating the chewing gum and the generation of the standard curve allows for using the number of microorganisms on the surface of the chewing gum to extrapolate the total number of microorganism contained on and within the chewing gum. One method of generating the calibration curve is to sonicate the chewing gum, wherein the gum is in standardized dimensions, such as chewing gum that was formed to a particular shape using a mold. This mold provides a fixed surface area for a given weight of chewing gum, so that the number of microorganisms attached to the surface of the chewing gum will serve as a means to calculate the number of microorganisms within the volume of chewing gum.

The mold may be any shape with standardized dimensions, for example the mold is a rectangle with dimensions of 15×15×4 mm or a cube with the dimensions 12 mm$^3$. The mold may be of any material, such as polytetrafluoroethylene (PTFE) also known as TEFLON or DYNEON, polyvinylindene fluoride (PVDF) also known as KYNAR, HYLAR and SOLEF; polyoxymethylene (POM) also known as DELRIN, CELCON, DURACON and HOSTAFORM; ethylene tetrafluorthylene (ETFE) also known as TEFZEL, polyamide-imides also known TORLON; perfluoroalkoxy (PFA) or fluorinated ethylene propylene (FEP).

The consistency of the calibration method was surprising and allows for accurate testing regardless of the type of bacteria contained on or within the chewing gum. For example, the experiments described in Example 1 use an in vitro finger chewing method. The invention also contemplates carrying out the invention using artificial or robotic chewing stimulators that reproduce mandibular movements exerted during mastication. Finger-chewing experiments accounted for approximately one log-unit less bacteria retrieved than actually chewed-in. Although the recovery is low, the same accounts for the numbers of bacteria that are lost in the process of finger-chewing, the majority are still trapped in the chewing gum cud. The calibration curve accounts for these losses and makes the estimation of the amount of bacteria that is trapped more accurate. Furthermore, the method of the invention only enumerates live microorganism that are cultivable. The consistency of the recovery is very high, e.g., a 10% recovery of bacteria from chewing gum was consistently observed for a wide range of concentrations. In the experiments described herein, rod-shaped *A. naeslundii*, displayed higher losses than coccalshaped strains, which can possibly be attributed to differences in adherence properties, since *A. naeslundii* is a bacteria known to have strong adherence to surfaces. When chewing gum contacts the oral cavity of mammal, microorganisms, such as bacteria, adhere to the chewing gum. Therefore, the methods of the invention can be used to detect the presence of a microorganism in the oral cavity of a mammal. The knowledge of the presence of certain microorganisms, such as bacteria, in an oral cavity can be used to diagnose an infection or other diseases or disorders of the oral cavity. In addition, the presence of certain microorganisms, such as certain bacteria, in the oral cavity may allow for the determination of the risk or susceptibility of a mammal for developing an infection disease or disorder of the oral cavity.

Chewing Gum

Chewing gum generally consists of a water insoluble gum base, a water soluble portion, and flavor. The water soluble portion dissipates with a portion of the flavor of the gum over a period of time during chewing. The gum base portion is retained in the mouth throughout the chew.

The insoluble gum base generally comprises elastomers, resins, fats and oils, softeners and inorganic fillers. The gum base may or may not include wax. The insoluble gum base can constitute approximately 5% to about 95% by weight of the chewing gum, more commonly the gum base comprises 10% to about 50% of the gum, and in some preferred embodiments approximately 25% to about 35% by weight, of the chewing gum.

For example, the chewing gum base of the present invention contains about 20% to about 60% by weight synthetic elastomer, about 0% to about 30% by weight natural elastomer, about 5% to about 55% by weight elastomer plasticizer, about 4% to about 35% by weight filler, about 5% to about 35% by weight softener, and optional minor amounts (about 1% or less by weight) of miscellaneous ingredients such as colorants, antioxidants, etc.

Synthetic elastomers may include, but are not limited to, polyisobutylene with gel permeation chromatography (GPC) weight average molecular weight of about 10,000 to about 95,000, isobutylene-isoprene copolymer (butyl elastomer), styrene-butadiene, copolymers having styrene-butadiene ratios of about 1:3 to about 3:1, polyvinyl acetate having GPC weight average molecular weight of about 2,000 to about 90,000, polyisoprene, polyethylene, vinyl acetate-vinyl laurate copolymer having vinyl laurate content of about 5% to about 50% by weight of the copolymer, and combinations thereof.

Preferred ranges for polyisobutylene are 50,000 to 80,000 GPC weight average molecular weight and for styrene-butadiene are 1:1 to 1:3 bound styrene-butadiene, for polyvinyl acetate are 10,000 to 65,000 GBC weight average molecular weight with the higher molecular weight polyvinyl acetates typically used in bubble gum base, and for vinyl acetate-vinyl laurate, vinyl laurate content of 10-45%.

Natural elastomers may include natural rubber such as smoked or liquid latex and guayule as well as natural gums such as jelutong, lechi caspi, perillo, sorva, massaranduba balata, massaranduba chocolate, nispero, rosindinha, chicle, gutta hang kang, and combinations thereof. The preferred synthetic elastomer and natural elastomer concentrations vary depending on whether the chewing gum in which the base is used is adhesive or conventional, bubble gum or regular gum, as discussed below. Preferred natural elastomers include jelutong, chicle, sorva and massaranduba balata.

Elastomer plasticizers may include, but are not limited to, natural rosin esters such as glycerol esters or partially hydrogenated rosin, glycerol esters of polymerized rosin, glycerol esters of partially dimerized rosin, glycerol esters of rosin, pentaerythritol esters of partially hydrogenated rosin, methyl and partially hydrogenated methyl esters of rosin, pentaerythritol esters of rosin; synthetics such as terpene resins derived from alpha-pinene, beta-pinene, and/or d-limonene; and any suitable combinations of the foregoing. The preferred elastomer plasticizers will also vary depending on the specific application, and on the type of elastomer which is used.

Fillers/texturizers may include magnesium and calcium carbonate, ground limestone, silicate types such as magnesium and aluminum silicate, clay, alumina, talc, titanium oxide, mono-, di- and tri-calcium phosphate, cellulose polymers, such as wood, and combinations thereof.

Softeners/emulsifiers may include tallow, hydrogenated tallow, hydrogenated and partially hydrogenated vegetable oils, cocoa butter, glycerol monostearate, glycerol triacetate, lecithin, mono-, di- and triglycerides, acetylated monoglycerides, fatty acids (e.g. stearic, palmitic, oleic and linoleic acids); and combinations thereof. Colorants and whiteners may include FD&C-type dyes and lakes, fruit and vegetable extracts, titanium dioxide, and combinations thereof. The base may or may not include wax.

In addition to a water insoluble gum base portion, a typical chewing gum composition includes a water soluble bulk portion and one or more flavoring agents. The water soluble portion can include bulk sweeteners, high-intensity sweeteners, flavoring agents, softeners, emulsifiers, colors, acidulants, fillers, antioxidants, and other components that provide desired attributes.

Softeners are added to the chewing gum in order to optimize the chewability and mouth feel of the gum. The softeners, which are also known as plasticizers and plasticizing agents, generally constitute between approximately 0.5% to about 15% by weight of the chewing gum. The softeners may include glycerin, lecithin, and combinations thereof. Aqueous sweetener solutions such as those containing sorbitol, hydrogenated starch hydrolysates, corn syrup and combinations thereof, may also be used as softeners and binding agents in chewing gum.

Bulk sweeteners include both sugar and sugarless components. Bulk sweeteners typically constitute about 5% to about 95% by weight of the chewing gum, more typically, about 20% to about 80% by weight, and more commonly, about 30% to about 60% by weight of the gum. Sugar sweeteners generally include saccharide-containing components commonly known in the chewing gum art, including but not limited to, sucrose, dextrose, maltose, dextrin, dried invert sugar, fructose, levulose, glactose, corn syrup solids, and the like, alone or in combination. Sugarless sweeteners include, but are not limited to, sugar alcohols such as sorbitol, mannitol, xylitol, hydrogenated starch hydrolysates, maltitol, and the like, alone or in combination.

High potency sweeteners can also be used, alone or in combination, with the above. Preferred sweeteners include, but are not limited to, sucralose, aspartame, salts of acesulfame, altitame, saccharin and its salts, cyclamic acid and its salts, glycerrhizinate, dihydrochalcones, thaumatin, lo han guao, monellin, stevia and its glycosides and the like, alone or in combination. In order to provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coacervation, and fiber extension may be used to achieve the desired release characteristics.

Combinations of sugar and/or sugarless sweeteners may be used in chewing gum. Additionally, the softener may also provide additional sweetness such as with aqueous sugar or alditol solutions.

The invention provides for methods of detecting of detecting microorganisms contained on or within polymers malleable in a living organism. In addition, the invention provides for methods of determining the microbe profile of a sample of saliva from a living organism. A profile of the microbes of a saliva sample may be used to determine susceptibility or risk of the organism for developing dental caries or periodontal disease regardless if the microbes are currently causing an infection. Furthermore, the methods of the invention may be used for quality control methods to determine if a polymer is susceptible or resistant to attachment or entrapment of microbes.

Microorganisms

The invention provides for methods of detecting, identifying and quantitating microorganisms contained on or within chewing gum. The term "type of microorganism" refers to a single family, genus, species, strain, serotype or serogroup of a particular microorganism depending on identification method.

"Microorganisms" or "microbes" refer to microscopic organisms which may be single celled or multicellular organisms, and may by pathogenic or commensal to the host organism. The invention provides for methods of detecting and quantitating microorganisms contained on and within a polymer that is malleable in a living organism and these microorganisms include bacteria, viruses, fungi and protozoa.

For example, the invention provides for methods of detecting, identifying and quantitating bacteria contained on or within chewing gum. The term "type of bacteria" refers to a single family, genus, species, strain, serotype or serogroup of bacteria depending on identification method.

The bacteria may be gram negative or gram positive bacteria, and anaerobic or aerobic bacteria. The bacteria may be a cocci (spherical) or bacilli (rod-shaped). The invention particularly contemplates methods of detecting oral bacteria such as commensal oral bacteria and pathogenic oral bacteria such as streptococci, lactobacilli, staphylococci, corynebacteria, *actinomcyes* sp., *fusobacterium* sp. and various anaerobes in particular bacteroides. Exemplary oral bacteria include *Streptococcus mutans, Streptococcus oralis, Streptococcus salivarius, Actinomyces naeslundii, Streptococcus sanguinis, Porphyromomas gingivalis, Porphymomas intermedia, Bacteroides forsythus, Tanneraella*.

The invention also provides for methods of detecting, identifying and quantitating viruses attached to chewing gum. The term "type of virus" refers to a single family, genus, species, strain, serrotype or serogroup of virus depending on identification method.

The virus may be a member of the Herpesvirus family such as the Human Herpes Virus (HHV) including HHV-1 (also known as herpes simplex virus (HSV)-1), HHV-2 (HSV-2), HHV-3 (also known as varicella-zoster virus), HHV-4 (Epstein-Barr virus), HHV-5 (cytomegalovirus), HHV-6, HHV-7 and HHV-8.

The virus may be a member of the Picornaviridae family (Enterovirus genus) such as poliovirus, group A coxsackievirus, group B coxsackievirus, echovirus. In particular, the virus may cause hand-foot-mouth disease such as coxsackievirus A16, A5, A7, A10, B2 and B5, a virus that causes herpangina such as coxsackievirus A1-6, A8, A10, and A22 and Enterovirus 71 (EV-71).

The virus may be a member of the Papovaviridae family such as the Human Papillomavirus family (HPV) including HPV-16, HPV-18, HPV-33 and HPV-35. The virus may be a member of the Paramyoxvirus family (Rubularivurs genus) such as mumps virus, Newcaastle disease virus, human parainfluenza virus type 2, 4a and 4b. The virus may be a member of the Paramyxovirus family (Morbillivirus genus). In addition, the virus may be a member of the Togavirus family (Rubivirus genus). The virus may be also be canine oral Papilloma virus, feline calicivirus, and feline herpesvirus The virus may also be an influenza virus such as human influenza virus A such as H1N1 and H3N3, human influenza virus B and human influenza virus C. The virus can be a virus that causes the common cold such as rhinovirus.

Certain herpes viruses (herpes simplex and varicella-zoster virus, the cause of chickenpox and shingles) are known causes of gingivitis. Other herpes viruses (cytomegalovirus and Epstein-Barr) may also play a role in the onset or progression of some types of periodontal disease, including aggressive and severe chronic periodontal disease. All herpes viruses go through an active phase followed by a latent phase and possibly reactivation. These viruses may cause periodontal disease in different ways, including release of tissue-destructive cytokines, overgrowth of periodontal bacteria, suppressing immune factors, and initiation of other disease processes that lead to cell death.

The invention provides for methods of detecting, identifying and quantitating a fungus attached to chewing gum. The term "type of fungus" refers to a single family, genus, species, strain, serotype or serogroup of fungus depending on identification method.

The methods of the invention may detect a fungus such as *Candida* e.g. *Candida albicans, Aspergillus, Cryptococcus neoformans, Cryptococcus gattii, Histoplasma capsulatum, Blastomyces dermatitidis, Paracoccidioides brasiliensis, Coccidiodes immites* and *Zygomycota*.

The invention provides for methods of detecting, identifying and quantitating a protozoa attached to chewing gum. The term "type of protozoa" refers to a single family, genus, species, strain, serotype or serogroup of protozoa depending on identification method.

The methods of the invention may detect protozoa such as *Entamoeba gingivalis* and *Trichomonas tenax*.

The invention contemplates detecting microorganisms that cause or are related to oral diseases and disorders such as periodontal disease (inflammation or infection of gum tissue) such as chronic periodontitis and acute adult periodontitis, gingivitis, such as acute necrotizing ulcerative gingivitis, Vincent angina, dental caries, herpesvirus infection, primary herpetic gingivostomatitis, or oral herpes (cold sores and canker sores), genital herpes, varicella-zoster virus infection e.g. chicken pox or shingles, influenza, common cold, venereal disease, mononucleosis, coxsackievirus infection such as hand-foot-mouth disease, herpangina, acute lymphonodular pharyngitis, mumps, measles (reubeola), rubella (German measles), African Burkitt lymphoma, nasopharyngeal carcinoma, oral hairy leukoplakia, roseola infantum, Karposi sarcoma, Candidiasis, acute pseudomemranous candidosis (thrush), acute atrophic (erythematous) candidosis, chronic hyperplastic candidosis, and chronic atrophic (erythematous) candidosis, aspergillosis, cryptococcosis, Histoplasmosis (also known as Cave disease, Darling's disease, Ohio valley disease, Reticuloendotheliosis, Spelunker's Lung and Caver's disease, Blastomycosis (also known as North American blastomycosis, Blastomycetic dermatitis, and Gilchrist's disease) Paracoccidioidomycosis (also known as Brazilian blastomycosis, South American blastomycosis, Lutz-Splendore-de Almeida disease and Paracoccidioidal granuloma), mucormycosis (after Mucorales), phycomycosis (after Phycomycetes) and basidiobolomycosis (after Basidiobolus) and zygomycosis (mucormycosis). The invention also provides for methods of diagnosing any condition, disease or disorder that are caused by or related to the presence of a microorganism contained on or within chewing gum.

Microorganism Colonies

In one embodiment of the invention, the methods comprising depositing the suspension of microorganism, such as bacteria, virus, protozoa or fungi on a solid support such as media comprising agar or another inert solidifying agent such as gelatin. The degree of solidification can also vary, with stiff agar being preferred to inhibit "swarming" and semi-solid or "sloppy" agar being used to observe other characteristics. Before utilization, such medium is preferably sterile.

The solid support may be a slant, stable or petri dish comprising the solid media. The solid medium has physical structure which allows bacteria to grow in physically informative or useful ways such as in colonies or in streaks. The term "colony" refers to the pile or mass of cells or organisms growing on or in solid medium. The invention contemplates that the solid media may comprise a colorimetric indicator, be selective media or differentiation media.

The nutrient media utilized in the invention is any liquid or solid preparation suitable for the growth, maintenance, storage, differential, isolation and/or identification of bacteria. These include those utilized for the initiation of a culture (or subculture), for enrichment, or for diagnostic (identification) tests of various organisms. These are tests in which the identity of a given organism may be deduced from the characteristics of its growth in or on particular media.

Selective media refers to media designed to suppress the growth of some microorganisms while allowing the growth of other microorganisms. For example, MacConkey agar selects against gram-positive bacteria, eosin-methylene blue agar selects against gram-positive bacteria and phenyethyl alcohol again selects against gram-negative bacteria. Differential media allow the growth or more than one microorganism of interest but with morphologically distinguishable colonies. For example, mannitol salts agar (mannitol fermentation=yellow), blood agar (various kinds of hemolysis), MacConkey agar (lactose fermentation=yellow) and eosin-methylene blue agar (various kinds of differentiation).

For anaerobic bacteria, the culture requires an oxygen-free gaseous above the surface of the medium and a medium free from dissolved oxygen. Even under these conditions, some anaerobes may not grow unless the medium has been pre-reduced, i.e. poised at or below a particular redox potential. Consequently, reducing agents, such as those containing sulfhydryl groups (e.g., $H_2S$, cysteine, thioglycollate) may also be included in the medium composition. Examples of commonly available medium being suitable for use for the selective growth of anaerobes is in the present invention, include, but are not limited to, Brain Heart Infusion, Brucella, CDC Anaerobe, Nutrient, Schaedler, Thioglycollate or Trypticase Soy. These are in both broth or agar form.

Additionally, the medium may be made anaerobic in an anaerobic jar, chamber or bag. An anaerobic jar is a container used for the incubation of materials (e.g. inoculated media) in the absence of oxygen or, in general, under gaseous conditions other than atmospheric. These are commonly known under the designations "Brewer Jar", "Gaspak", "McIntosh and Filde's Anaerobic Jar", etc.

The culture medium is inoculated with a sample of the suspension of the bacteria removed from the chewing gum. The suspension may be diluted prior to inoculating the culture medium or applying to the solid support. In certain embodiments, the sample may be serially diluted and the serial dilutions used to inoculate a plurality of culture media in order to obtain a more precise enumeration of bacteria in the original sample.

In another embodiment of the invention, the methods comprise growing the bacteria removed from the chewing gum and broth media may be inoculated with the diluted suspension of bacteria removed from the chewing gum. Broth media refers to media lacking solidifying matrix. The inoculated culture medium is incubated under conditions that permit the growth of bacteria. The broth media may allow for the detection of the type of media. For example, the media comprises a colorimetric indicator, selective media or differential bacteria.

In some embodiments of the method of the present invention, the number of microorganisms present in the sample may be enumerated. For example, one may enumerate the number of bacteria in a sample by selecting a form of culture medium that permits the formation of colonies. After the culture medium is inoculated and incubated under conditions that permit colonies of the bacteria to form, the colonies may be counted. Colonies may be counted by counting the detectable signal generated by reaction of the indicator and phosphatase produced by the bacteria. In embodiments in which the phosphatase substrate indicators 5-bromo-6-chloro-3-indolylphosphate or 6-chloro-3-indolylphosphate are employed, the detectable signal may include red to red-violet colored colonies. Thus, in certain embodiments, enumeration of microorganism includes merely counting the particular color colonies such as the red to red-violet colonies under phosphate conditions. Suitable detectable signals include but are not limited to a chemiluminescent signal, a fluorescent signal, or a change in electrical conductivity. In some embodiments, detection of the detectable signal may be accomplished manually, while in other embodiments detection of the detectable signal may require specialized detection instrumentation known to those of ordinary skill in the art. The method used to enumerate microorganisms in a particular sample may depend, at least in part, on the type of detectable signal used in the method of the present invention.

In addition to quantifying the microorganisms removed from the chewing gum, the method of the invention may be used to identify the microorganism removed from the chewing gum. The identification may be based on taxonomic principles based on morphologic and metabolic characteristics. Colony morphology may be analyzed to identify the type of bacteria removed from the chewing gum. The term "colony morphology" refers to the visual characteristics of a colony. Colonies that differ in appearance are typically different bacterial family, genus, species, strain, serotype or serogroup. Colony morphology is evaluated based on the colony shape, margin, color, surface features, elevation, light transmission or pigmentation to name a few.

There are many different tests known in the art which distinguish microorganisms. Molecular biology techniques used for the identification of specific genes or gene segments of known bacteria include PCR, northern blotting, conventional and pulsed-field Southern blot, denaturing gradient gel electrophoresis, microarrays, slot blotting or dot blotting using polynucleotide sequences specific for a specific family, genus, species, strain, serotype or serogroup.

For example, determining the sequence of the 16S rRNA and other regions within the bacterial genome may be used to identify a type of bacteria. Analytical chemistry techniques such as determining fatty acid profiling, carbohydrate profiling and ubiquinone profiling, characterization of secreted metabolic products such as volatile alcohols and short chain fatty acids are also used to identify at type of bacteria.

In another embodiment of the invention, the methods comprising depositing the suspension of virus on a confluent monolayer of cells affixed within a solid support such as media comprising agar, caboxylmethyl cellulose or another inert solidifying agent such as gelatin as described above. The viral colonies are also known as "viral plaque." The viral plaque is formed when the virus infects a cell within the fixed monolayer. The virus will lyse the cell and the infection will spread to other cells. The infected cells create a plaque which can be visually seen with a microscope. Assays for determining a quantity of virus are well known in the art such as those that utilize immunofluorescence, colorimetric measurement, proteins and hemagglutination, see e.g., Kaufman & Kabelitz, *Methods of Microbiology* Vol. 32 Immunology of Infection, Academic Press, 2002.

In addition to quantifying the virus removed from the chewing gum, the methods of the invention may be used to identify the virus removed from the chewing gum. The identification may be based on molecular biology techniques used for the identification of specific genes or gene segments of known viruses include PCR, northern blotting, conventional and pulsed-field Southern blot, denaturing gradient gel electrophoresis, microarrays, slot blotting or dot blotting using polynucleotide sequences specific for a specific family, genus, species, strain, serotype or serogroup. Microscopy may be also used to identify morphological characteristics of the virus, such as the observing the size, shape or other distinct morphological features of the virus.

Kits

The invention also provides for kits to carry out the methods of the invention. In particular, the invention provides for kit comprising components for detection and/or quantification of a bacteria removed from chewing gum according to any of the method of the invention.

Other aspects and advantages of the present invention will be understood upon consideration of the following illustrative example.

EXAMPLES

Example 1

Quantification of Bacteria Adhered to Finger Chewed Gum

An in vitro finger chewing study was carried out to quantify the bacteria adhered to or within the chewing gum. Two commercially available spearmint chewing gum tabs were used in the experiment:

Gum A: Commercial spearmint gum 1 (1.5 g tabs)) Composition in descending order of predominance by weight: Sorbitol, gum base, glycerol. Natural and artificial flavors; less than 2% of: Hydrogenated starch hydrolysate, aspartame, mannitol, acesulfame K, soy lecithin, xylitol, beta-carotene, blue 1 lake and butylated hydroxytoluene.

Gum B: Commercial spearmint gum 2 (1.5 g tabs). Composition in descending order of predominance by weight: Sorbitol, gum base, glycerin, mannitol, xylitol. Natural and artificial flavors; less than 2% of: Acesulfame K, aspartame, butylated hydroxytoluene, Blue 1 Lake, soy lecithin and yellow 5 lake. All gum pieces had a standard weight of 1.5 g.

Three different bacterial strains were used for this study, *S. oralis* J22, *S. mutans* ATCC 25175 and *A. naeslundii* T14V-J1. *S. oralis* and *A. naeslundii* are considered initial colonizers of tooth surfaces in vivo, while *S. mutans* is causative to dental caries. Streptococci were grown aerobically in Todd Hewitt Broth at 37° C. and *Actinomyces* were grown anaerobically in Brain Heart Infusion. Bacteria were first grown on appropriate agar plates from a frozen stock for 24 hours after which 5 ml of the appropriate culture medium was inoculated for 24 hours. A main culture was prepared with a 1:10 dilution in fresh medium for 16 hours. Main cultures were sonicated to suspend bacterial aggregates. The bacterial concentration was determined using the Bürker Türk counting chamber and concentrations were adjusted to $10^4$, $10^5$, $10^7$ and $10^9$ bacteria per ml.

For each strain, bacteria were finger-chewed into a gum tablets by adding 1.5 g of a chewing gum together with 200 µl of a bacterial suspension into the finger of a sterile latex glove (Powder-Free Latex Examination Gloves, VWR international, Radnor, USA). Next, bacteria were finger-chewed into the gum in a water bath at 30° C. for 5 minutes. After finger-chewing, the gum was removed from the finger, dipped once in sterile water and put into a Teflon mold (15×15×1 mm) to create a reproducible surface area of the gum (±15×15×4 mm) using a sterile pair of tweezers. Subsequently, bacteria were removed from the gum by sonication in sterile polystyrene cups filled with 5 ml filter sterile (Millipore, Millex GS 0.22 µm) Reduced Transport Fluid (RTF) as described in Syed et al. (*Appl. Microbiology* 24: 638-644) for 60 seconds in a water bath sonicator (ELMA Transsonic TP690, Elma GmbH & Co, Germany). Finally, the resulting suspension was serially diluted and plated on Todd Hewitt Broth (THB) agar or blood agar plates (Bloodagar base no. 2, 40 g/L, Hemin 5 mg/L, Menadion 1 mg/L, sheep blood 50 ml/L). Colony Forming Units (CFUs) at 37° C. for 48 hours after which the number of colony-forming units were counted and converted to numbers of bacteria trapped in a single gum tab. Experiments were carried out in triplicate.

To account for possible loss of bacteria due to adhesion to the inner surface of the glove surface, the glove finger was turned inside/out, sonicated in 10 ml filter sterile RTF for 60 seconds and serial dilutions plated on agars as described above after which the numbers of CFUs possibly lost were determined. Similarly, the water in which the finger-chewed gum was dipped in (see above) was analyzed for bacterial losses. During finger-chewing, approximately 0.05 log units of coccal bacteria (*S. oralis* and *S. mutans*) were lost due to adhesion to the glove surface. *A. naeslundii* adhered in slightly higher numbers to the glove surface. Bacterial losses due to dipping the finger-chewed gum tabs in water amounted on average 0.004 log-units. Losses during finger chewing were irrespective of gum involved, however slightly decreased with rising concentration.

Accordingly, since different numbers of bacteria were finger-chewed into the gum samples, a calibration curve could be made using the number bacteria retrieved from each gum for the different bacterial strains versus the actual number of bacteria trapped in the finger-chewed gums. The calibration curve allows for the calculation of the amount of bacteria attached or entrapped within to the finger-chewed or masticated chewing gum and which reflects the total amount of microorganisms attached to and within the chewing gum.

Figure 1:
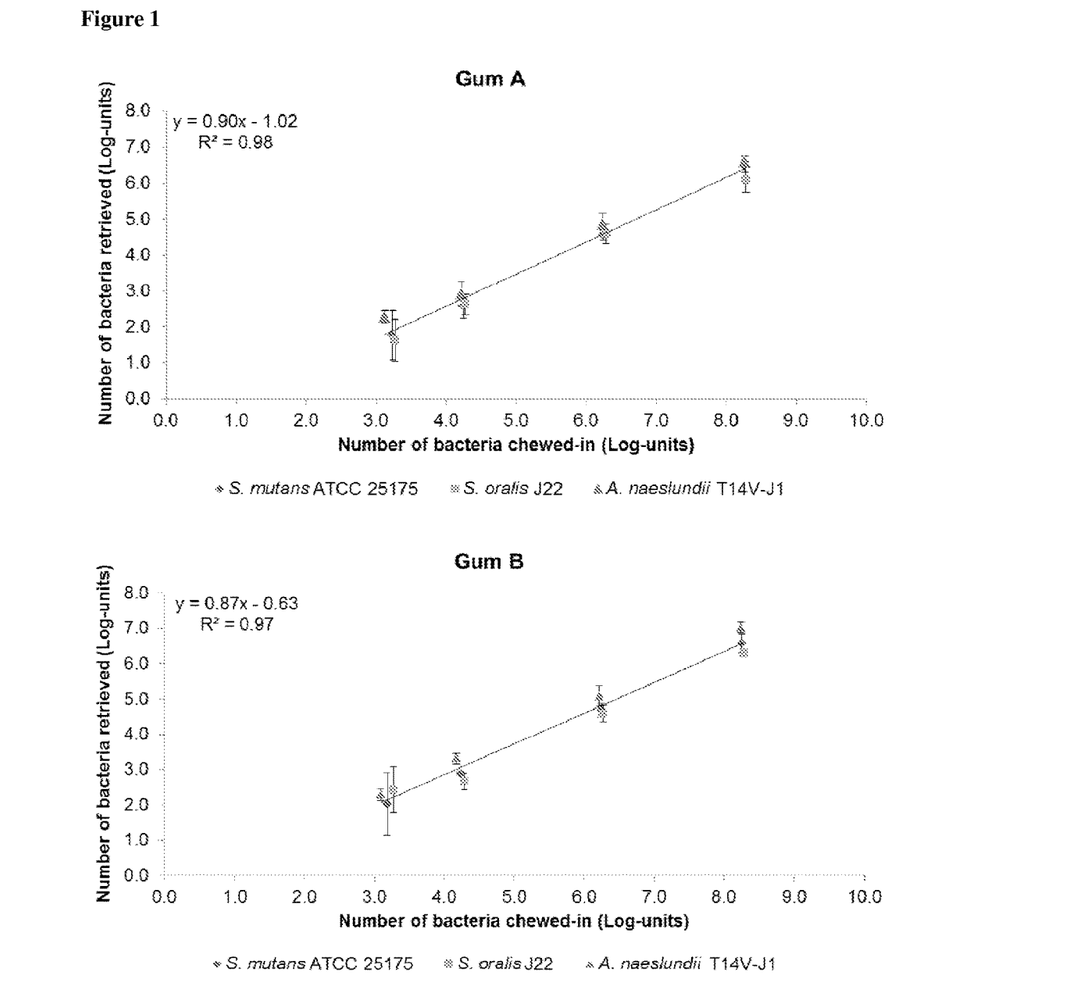
Figure 2:
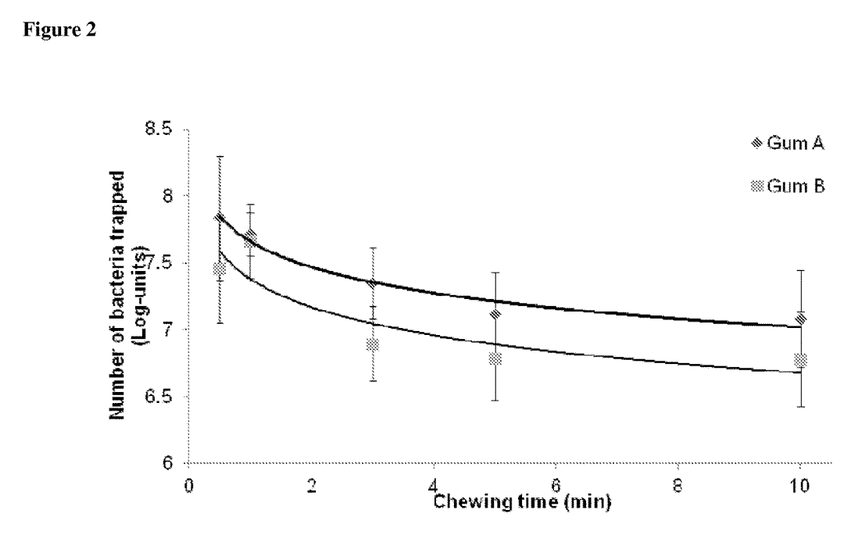
FIG. 2 provides the number of bacteria entrapped in chewing gum as a function of time, expressed either in colony forming unites (CFUs; log-units) determined using the calibration curve.

Accounting for these losses, linear relations were obtained between the numbers of bacteria retrieved from a gum and the number of bacteria finger-chewed in (FIG. 1), that were independent of the bacterial strain or gum type involved. As sonication can only release bacteria trapped in a gum from the outer surface, the number of bacteria retrieved was roughly 1.5 log-unit less than chewed in.

This study is further evidence that the methods of the invention can detect and quantify oral bacteria that is contained on and within chewing gum.

Example 2

Quantification of Bacteria Adhered to In Vivo Chewed Gum

An in vivo study was carried out to demonstrate that chewing gum can remove bacteria from the oral cavity. Healthy human volunteers give their written informed consent to participate in the study. Inclusion criteria for the study was that each volunteer be good health and have their permanent teeth with at least 16 natural elements. An exclusion criterion was the use of antibiotics or mouth rinse in the month prior to the study. Furthermore, volunteers did not use antibiotics, mouth rinse and other chewing gum types during the study. All experiments were carried out in duplicate.

Next, volunteers were asked to chew two different gum types for varying amounts of time up to 10 minutes and the number of bacteria chewed into the chewing gum were determined in terms of CFUs using sonication of chewed gum tabs in standardized dimensions. Determination of numbers of bacteria, yielded an initial peak of bacteria attached shortly after chewing. As chewing time increased, up to 10 minutes, bacterial attachment decreased Numerous modifications and variations in the practice of the invention are expected to occur to those skilled in the art upon consideration of the presently preferred embodiments thereof. Consequently, the only limitations which should be placed upon the scope of the invention are those which appear in the appended claims.

What is claimed:

1. A method of quantitating microorganisms contained on and within chewing gum, the method comprising
    a) sonicating the chewing gum under conditions which remove the microorganism from the chewing gum and deposit the microorganism in a suspension,
    b) contacting at least a portion of the suspension with a solid-support under conditions that promote colony formation, and
    c) quantitating the colonies formed on the solid-support, wherein the number of colonies indicates the total quantity of microorganisms selected from the group consisting of bacteria, virus, fungus and protozoa, contained on and within the chewing gum.

2. The method of claim 1, wherein the sonication is carried out in standardized dimensions.

3. The method of claim 1, further comprising the step of generating a standard curve to determine the quantity of microorganisms contained on and within the chewing gum.

4. The method of claim 1, wherein the bacteria is *Streptococcus mutans, Streptococcus oralis, Actinomyces naeslundii, Streptococcus sanguinis, Porphyromomas gingivalis, Porphymomas intermedia, Bacteroides forsythus, Tanneraella forsythia, Campylobacter rectus, Eubacerium nodatum, Peptostreptococcus micros, Streptococcus intermedius, Aggregetibacter actinomycetemcomitans, Treponema denticola, Lactobacillus, Eikenella corrodens, Capnocytophaga gingivalis, Streptococcus gordonii, Veillonella parvula, Fusobacterium nucleatum, Prevotella intermedia, Lactobacillus salivarius, Streptococcus salivarius* and *Streptoococus sobrinus*.

5. The method of claim 1, further comprising the step of diagnosing an infection in a mammalian subject,
    wherein the chewing gum was in contact with the oral cavity of the subject, and
    wherein the presence of a microorganism contained on or within the chewing gum is indicative of a infection in the subject.

6. An in vitro method of diagnosing an infection in the oral cavity of a mammalian subject, the method comprising detecting a microorganism contained on or within the chewing gum according to the method of claim 1,
    wherein the chewing gum was in contact with the oral cavity of the subject, and wherein the presence of the microorganism in the oral cavity is indicative of a bacterial infection in the subject.

7. An in vitro method of determining the susceptibility of a mammalian subject for developing an infection in the oral cavity, the method comprising
   detecting a microorganism according to the method of claim 1,
   wherein the chewing gum was in contact with the oral cavity of the mammal, and
   wherein the presence of the microorganism in the oral cavity is indicative of increased susceptibility for an infection in the subject.

8. The method claim 7, wherein the method further comprises the steps of
   c) comparing the microorganism profile of the mammalian subject with a reference microorganism profile,
   wherein the reference profile is indicative for increased susceptibility for a disease or disorder of the oral cavity, and
   d) scoring the microorganism profile to determine whether the subject has increased susceptibility for a disease or disorder of the oral cavity.

9. The method of claim 7, further comprising the step of quantitating the microorganisms contained on or within the chewing gum.

10. The method of claim 7, further comprising generating a standard curve to quantify the microorganisms.

11. The method of claim 8, wherein the bacteria is *Streptococcus mutans, Streptococcus oralis, Actinomyces naeslundii, Streptococcus sanguinis, Porphyromomas gingivalis, Porphymomas intermedia, Bacteroides forsythus, Tanneraella forsythia, Campylobacter rectus, Eubacerium nodatum, Peptostreptococcus micros, Streptococcus intermedius, Aggregetibacter actinomycetemcomitans, Treponema denticola, Lactobacillus, Eikenella corrodens, Capnocytophaga gingivalis, Streptococcus gordonii, Veillonella parvula, Fusobacterium nucleatum*, and *Streptoococus sobrinus*.

* * * * *